(12) United States Patent
Wainer

(10) Patent No.: US 6,723,988 B1
(45) Date of Patent: Apr. 20, 2004

(54) HAND-HELD GAMMA CAMERA

(75) Inventor: Naor Wainer, Zichron-Yaakov (IL)

(73) Assignee: Elgems Ltd., Tirat-Hacarmel (IL)

( * ) Notice: Subject to any disclaimer, the term of this patent is extended or adjusted under 35 U.S.C. 154(b) by 0 days.

(21) Appl. No.: 10/420,473

(22) Filed: Apr. 22, 2003

Related U.S. Application Data

(62) Division of application No. 09/378,871, filed on Aug. 23, 1999, now Pat. No. 6,587,710.

(30) Foreign Application Priority Data

Jun. 6, 1999 (IL) .................................................. 130317

(51) Int. Cl.⁷ .............................................. G01T 1/166
(52) U.S. Cl. .............................. 250/336.1; 250/370.01; 250/361 R
(58) Field of Search .......................... 250/336.1, 361 R, 250/363.02, 363.04, 370.01

(56) References Cited

U.S. PATENT DOCUMENTS

| | | | |
|---|---|---|---|
| 4,020,348 A | 4/1977 | Turcotte et al. | |
| 4,223,221 A | 9/1980 | Gambini et al. | |
| 4,245,646 A | 1/1981 | Ionnou et al. | |
| 4,672,207 A | 6/1987 | Derenzo | |
| 4,932,411 A | 6/1990 | Fritschy et al. | |
| 4,999,501 A | 3/1991 | Lacy | |
| 5,672,877 A | 9/1997 | Liebig et al. | |
| 5,777,332 A | * 7/1998 | Lonn et al. | 250/363.04 |
| 5,813,985 A | 9/1998 | Carroll | |
| 5,871,013 A | 2/1999 | Wainer et al. | |
| 5,974,165 A | 10/1999 | Giger et al. | |
| 6,177,675 B1 | 1/2001 | Gagnon et al. | |

FOREIGN PATENT DOCUMENTS

| | | |
|---|---|---|
| WO | WO 98/23974 | 6/1987 |

* cited by examiner

*Primary Examiner*—Constantine Hannaher
*Assistant Examiner*—Timothy Moran
(74) *Attorney, Agent, or Firm*—Fenster & Company

(57) ABSTRACT

A radiation camera system, comprising:
  a freely positionable radiation camera;
  a spatial coordinate determining system that determines the coordinates of the camera; and
  a receiver which receives the spatial coordinate information and imaging information, generated by the camera and provides imaging information referenced to a coordinate system not fixed in the camera.

21 Claims, 3 Drawing Sheets

HAND-HELD GAMMA CAMERA

RELATED APPLICATIONS

This application is a divisional of U.S. application Ser. No. 09/378,871, filed on Aug. 23, 1999 now U.S. Pat. No. 6,587,710.

FIELD OF THE INVENTION

The present invention relates generally to hand-held gamma cameras and in particular to a hand-held gamma camera with a remotely readable spatial position measurement.

BACKGROUND OF THE INVENTION

Generally, in nuclear imaging, a radioactive isotope is injected to, inhaled by or ingested by a patient. The isotope, provided as known as a radioactive-labeled pharmaceutical (radio-pharmaceutical) is chosen based on bio-kinetic properties that cause preferential uptake by different tissues. The gamma or beta photons emitted by the radio-pharmaceutical are detected by radiation detectors outside the body, giving its spatial uptake distribution within the body, with little trauma to the patient.

FIG. 1 illustrates a general nuclear-imaging detector 10 comprising a NaI(Tl) scintillation crystal 12. Generally, scintillation crystal 12, of a diameter $D_1$, is large enough to image a significant part of the human body (typically 40 cm). An array of photo-multiplier tubes (PMTs) 14 view scintillation crystal 12, to give positional sensitivity. Each PMT 14 has an x and a y coordinate. When a photon is absorbed by scintillation crystal 12, light is generated. A number of PMTs 14 receive the light and produce signals. The X and Y coordinates of the event are determined by the strength of the signals generated by each PMT. The energy of the event is proportional to the sum of the signals, called the Z signal. Only Z signals within a given range are counted.

Size is a basic drawback of the multiple PMTs detector system. The basic limiting size of a PMT is too large for multiple PMTs to be fitted in a small camera. An alternative system using an NaI(Tl) scintillation crystal, backed by a single, position sensitive PMT, can be substantially smaller, but the field of view is small.

Semiconductors with high atomic numbers and relatively high densities such as CdZnTe, CdTe, $HgI_2$, InSb, Ge, GaAs, Si, PbCs, PbCs, PbS, or GaAlAs, have a high stopping power and can be used as gamma ray detectors with good photon detection efficiencies, good spatial resolution, and a relatively high photon-energy resolution. Solid state semiconductor gamma cameras generally comprise arrays of pixelated detector, hereinafter referred to as "pixelated detectors". One type of pixelated detector is described in PCT publication WO 98/23974, the disclosure of which is incorporated herein by reference. FIG. 2 shows a typical construction of a pixelated detector 20 comprising a crystal 22 formed from a semiconductor material such as one of those noted above. A face 24 of crystal 22 has a large single cathode electrode 26. An opposite face 28 of crystal 22 has an anode 30 comprising a rectangular array of identical small square anode pixels 32. Typically, sizes of anode pixels 32 vary between 1 and 4 $mm^2$, and the thickness of crystal 22, between anode 30 and cathode 26 is on the order of millimeters to a centimeter. In operation, a voltage difference is applied between anode and cathode so that an electric field, hereinafter referred to as a "detector field", is generated in crystal 22. This field is typically on the order of a few kilovolts per centimeter.

When a photon, having an energy typical of the energies of photons used in gamma cameras, is incident on crystal 22, it generally loses all its energy in crystal 22 by ionization and produces pairs of mobile electrons and holes in a localized region of crystal 22. As a result of the detector field, the holes drift to cathode 26 and the electrons drift to anode 30, thereby inducing charges on anode pixels 32 and cathode 26. The induced charges on anode pixels 32 are sensed and generally partially processed by appropriate electronic circuits located in a detector base 34 to which detector 20 is mounted. Signals from the induced charges on pixels 32 are used to determine the time at which a photon is detected, how much energy the detected photon deposited in the crystal and where in the crystal the photon interaction took place.

An alternative solid-state detector system is described in U.S. Pat. No. 4,672,207 "Readout System for Multi-Crystal Gamma Cameras" by Derenzo. The detector system comprises an array of scintillation crystals arranged in N rows and M columns and adapted to be struck by gamma rays from a subject. A separate solid-state photodetector is optically coupled to each crystal. N+M amplifiers, connected to the photodetectors distinguish the particular row and column of an activated photodetector.

Another alternative solid state system comprises a single scintillation crystal, optically coupled to multiple photodetectors, wherein each photodetectors has a specific x, and y coordinate.

Generally, a collimator 16 is placed between scintillation crystal 12 or 22 and the tissue. Commonly, collimator 16 is honeycomb shaped, comprising a large number of holes separated by parallel lead septa. The purpose of collimator 16 is to intercept and eliminate gamma-ray photons that are not traveling in an accepted direction, parallel to the lead septa.

Small gamma cameras that are hand-held are known. Generally, they are based on solid-state detectors such as a pixelated detector. Alternatively, they comprises a single NaI(Tl) scintillation crystal and a single, position sensitive PMT.

Small cameras are especially useful for detecting beta radiation. Since beta rays are strongly absorbed by tissues, small cameras are able to reduce the distance between the radiation source and the camera, especially in the operating room.

A specific problem with hand-held garnrna cameras is spatial location of any suspected finding with respect to some known reference system, since the hand-held camera itself is not referenced to any coordinate system.

New radio pharmaceuticals enhance the need for minicameras for both beta and gamma radiation. These radio pharmaceuticals are based on peptides, FABs (fraction of antibody) or MAB (monoclonal antibodies) which are especially designed to attach themselves to receptors usually found in specific cancerous cells.

SUMMARY OF THE INVENTION

One aspect of some preferred embodiments of the present invention relates to providing a small radiation camera such as a gamma camera or beta camera with a preferably remotely readable spatial coordinate determining device that registers the coordinates of the camera, Preferably, the six orthogonal position and orientation coordinates. Preferably, the remote spatial coordinate device comprises two parts:

1. a transmitter which is attached to the camera, for example at the tip of the handle, and which transmits 3-D coordinate information, preferably continuously, during operation; and
2. a receiver at some remote location to the camera, for example on the ceiling, or near a data-acquisition computer, which receives the 3-D coordinate information sent by the transmitter.

In some preferred embodiments of this aspect, the remote spatial coordinate device is an optical device. Alternatively, it is based on radio positioning. Alternatively, it is a GPS like device (together with some means for measuring angles). Alternatively, it is based on microwaves. Alternatively coordinate determination is based on measurements of static, pulsed DC or AC magnetic fields. Alternatively, any remote spatial coordinate determining device known in the art. None of the above techniques or devices are new, per se, and therefore will not be discussed in detail herein. Many such devices are known in the art, and the present invention may utilize any suitable device.

In some preferred embodiments of this aspect, the remotely readable spatial coordinate determining device is connected to a data-acquisition computer and a display screen, preferably by a cable, so that information acquired by the gamma camera is displayed on screen in real time, with the spatial coordinates of any lesion. Alternatively, signals related to the coordinate determination may be carried by the same cable. Alternatively, both data and coordinate information may be transmitted to the computer by radio or optical communication means as known in the art.

In some preferred embodiments of this aspect, referencing between the coordinate system of the remotely readable spatial coordinate determining device and the patient is achieved by a second, stationary imaging system, such as an x-ray machine, a CAT scanner, an MRI machine, or any other imaging system as known in the art. Alternatively, the patient affected tissue may be marked with some visible, radioactive ink, which is imaged by the camera. In some preferred embodiments of the invention, a separate positioning system may be attached to the patient, so that the patient and the gamma camera are mutually referenced via the two positioning systems. Alternatively, the "stationary" reference for the transmitter may be attached (or referenced to) the patient.

In a preferred embodiment of the invention, the nuclear imaging information is superimposed on the X-Ray, MRI, ultrasound or other image.

In some preferred embodiments of this aspect, imaging a suspected finding from different viewing angles (with positions and orientations provided by the remotely readable spatial coordinate determining device) yields the three-dimensional location of a suspected lesion and allows its three dimensional reconstruction.

An aspect of some preferred embodiments of the present invention relates to providing a small invasive radiation camera with a remote spatial positioning device which may be used during operation to aid a surgeon in the location of suspected lesions. Preferably, the gamma camera is covered with a disposable, sterile, radiolucent condom-like cover. Preferably, information acquired by the radiation camera (or a planar or 3D reconstruction) is displayed on screen in real time, in the surgical room showing the location of any suspected lesion with respect to the patient's coordinates and/or structure. In some preferred embodiments of the invention, the camera is placed against the tissue.

Alternatively, a small gamma camera may image through the skin. Since the camera is small, it allows the physician to get closer to the lesion than with a large camera.

One particular advantage of such a camera is that it can give an indication as to whether all of a cancerous growth has been removed. In particular, before the growth is removed, the growth is imaged. After removal, an additional image of the same area is taken to determine if any of the tissue that took up the radiopharmaceutical remains in the body and where it is situated.

An aspect of some preferred embodiments of the present invention relates to providing a small radiation counter at the tip of the radiation camera (gamma or beta) as a coarse probe. Preferably, the radiation counter has a much higher efficiency than the spatially sensitive and energy sensitive detector of the camera. Therefore, the counter may lead the physician to areas that need close examination. This is especially helpful for beta cameras.

An aspect of some preferred embodiments of the present invention relates to providing a small gamma camera that is not hand-held; rather it is attached to an arm that descends from a gantry near or above the surgery table. The coordinates of the camera are then determined as described above or by other means.

As used herein, the term "freely positionable" means a device which can assume substantially any position and orientation. Such devices include hand held devices and devices mounted on articulated arms.

There is thus provided, in accordance with a preferred embodiment of the invention, a radiation camera system, comprising;

a radiation imager having a field of view and having a first radiation sensitivity; and a radiation detector having a sensitivity greater than that of the imager and facing in a same direction as a field of view of the camera.

There is further provided, in accordance with a preferred embodiment of the invention, a method of nuclear imaging comprising:

providing a radiation imager having a field of view and having a first radiation sensitivity and a radiation detector having a sensitivity greater than that of the imager and facing in a same direction as a field of view of the camera;

determining a direction for the imager based on a radiation signal from the detector.

Preferably, the method includes moving the imager toward a region to be imaged based on the strength and direction of radiation causing the detector radiation signal. Preferably, the direction is determined from a direction which gives a maximum radiation signal from the detector.

There is further provided, in accordance with a preferred embodiment of the invention, a method of determining whether a lesion which has been tagged with a radionuclide, has been removed, comprising:

acquiring a first nuclear image of an area including the cancerous lesion, prior to excision of the lesion;

acquiring a second nuclear image of the area after excision of at least part of the lesion; and comparing the first and second lesions to each other.

Preferably, the first and second radionuclide images are acquired during surgery. Preferably, the images are acquired using a camera situated within the surgical opening.

Preferably, the method includes determining the coordinates of a camera taking said images and utilizing said determined coordinates in making said comparison. Preferably, the image is acquired with an imaging face of the camera contacting body tissue.

there is further provided, in accordance with a preferred embodiment of the invention, a radiation camera system, comprising:

a freely positionable radiation camera;

a spatial coordinate determining system that determines the coordinates of the camera;

a receiver which receives the spatial coordinate information and imaging information, generated by the camera and provides imaging information referenced to a coordinate system not fixed in the camera.

Preferably, the system includes:

an image source;

image alignment circuitry that receives the imaging information and an image from the source and references the imaging information to the image from the source; and a display that displays a radiation image based on the imaging information and the image from the source.

Preferably, the radiation image and the image from the source are displayed on a same coordinate system.

In preferred embodiments of the invention the image from the source is a CT image, an MRI image or an ocular image.

In a preferred embodiment of the invention, the image from the source is a previous radiation image of a same portion of the patient.

In a preferred embodiment of the invention, the radiation camera a hand held camera.

In a preferred embodiment of the invention, the spatial coordinate information is determined by the measurement of magnetic fields.

In a preferred embodiment of the invention, the camera comprises sensors which measure electromagnetic fields generated by at least one fixed source to produce said spatial coordinate information. Preferably, the system includes a receiver to which said spatial coordinate information is transferred, wherein said information is transferred to said receiver by wireless means.

In a preferred embodiment of the invention, the imaging information is transferred to a receiver from the camera by wireless means.

In a preferred embodiment of the invention, the camera is a gamma camera. Alternatively, the camera is a beta camera.

In a preferred embodiment of the invention, the camera is an Anger camera.

In a preferred embodiment of the invention, the camera is a solid state camera.

In a preferred embodiment of the invention, the system includes a radiation detector having a sensitivity greater than that of the camera facing in a same direction as a field of view of the camera.

In a preferred embodiment of the invention, the spatial coordinate determining system includes a position sensor mounted on the camera.

In a preferred embodiment of the invention, the coordinate system is fixed in space.

In a preferred embodiment of the invention, the coordinate system is referenced to a patient.

BRIEF DESCRIPTION OF THE DRAWINGS

The present invention will be more clearly understood from the following detailed description of the preferred embodiments of the invention and from the attached drawings, in which same number designations are maintained throughout the figures for each element and in which.

DETAILED DESCRIPTION OF PREFERRED EMBODIMENTS

Figure 1:
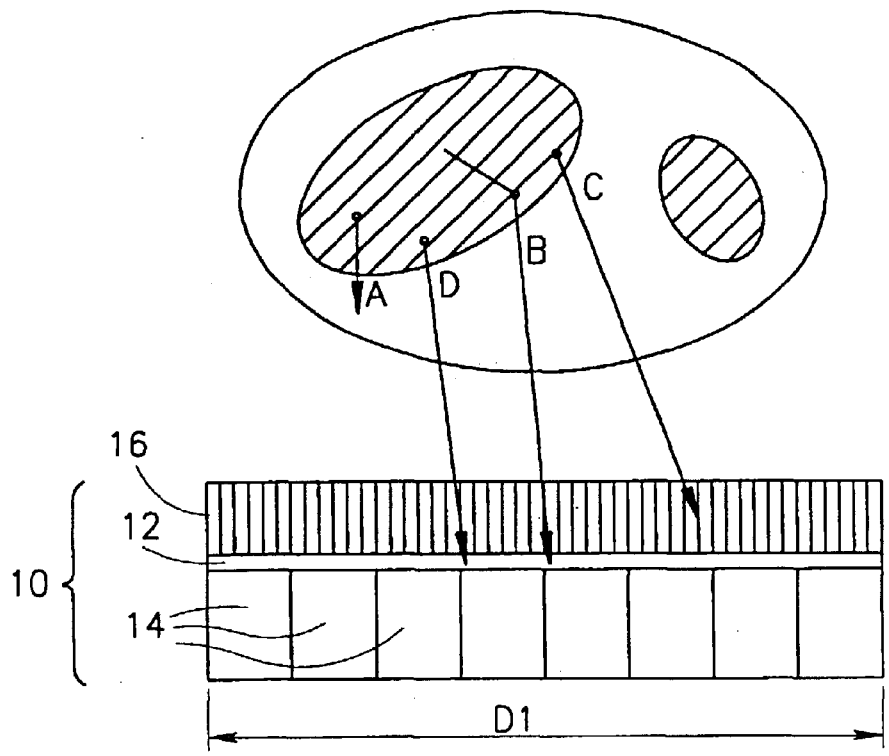
FIG. 1 is a schematic illustration of a nuclear-imaging detector, comprising an NaI(Tl) scintillation crystal, as known in the art.
Figure 2:
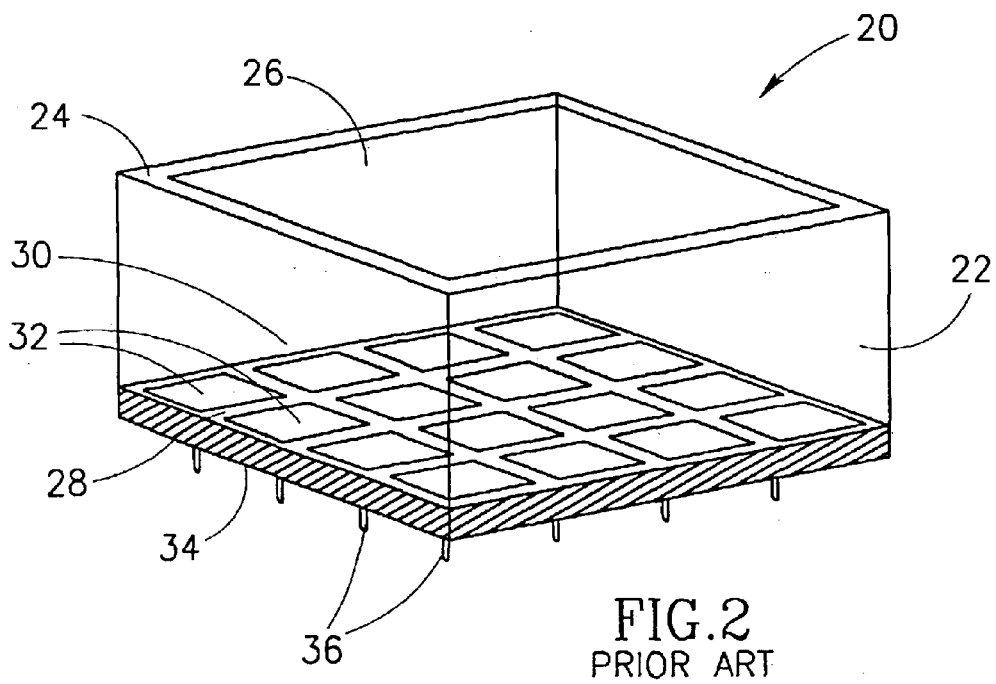
FIG. 2 is a schematic illustration of a pixelated, solid-state scintillation detector, as known in the art.
Figure 3:
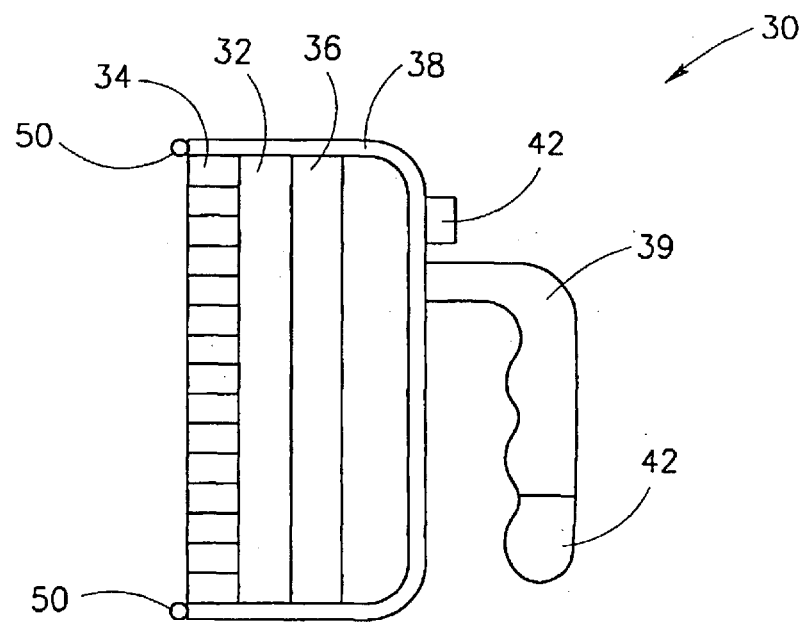
FIG. 3 is a schematic illustration of a small gamma camera with a remotely readable spatial coordinate determining device, in accordance with a preferred embodiment of the present invention.

Reference is now made to FIG. 3 which is a schematic illustration of a small gamma camera 30 with a remote spatial positioning device, in accordance with a preferred embodiment of the present invention. Preferably, gamma camera 30 comprises:

a scintillation detector 32 which detects photon radiation;

a collimator 34, which allows only gamma rays traveling in a certain direction to reach scintillation detector 32, attached to the side of scintillation detector 32 facing the skin;

a photon-position sensitive device 36, attached to scintillation detector 23 on its other side;

a rigid skeleton 38 which contains all the aforementioned parts;

a handle 39, attached to skeleton 38 for holding and manipulating gamma camera 30;

a coordinate transmitter 42, attached to rigid skeleton 38, either directly, or via handle 39; and a remote receiver 44 not physically attached to gamma camera 30, which receives the 3-D information sent by transmitter 42.

In some preferred embodiments of the present invention, gamma camera 30 is very small, and can be used in the open body of a patient, during surgery.

Transmitter 42 and remote receiver 44 which together make up remotely readable spatial coordinate determining device 36 may be any such device, known in the art.

Scintillation detector 32, collimator 34 and photon-position sensitive device 36, may be any scintillation detector, collimator and photon-position sensitive device, as known in the art. In some preferred embodiments, scintillation detector 32 and photon position sensitive device 36 are replaced by a pixelated solid-state detector. Alternatively, an NaI(Tl) or CsI(Tl)scintillation crystal coupled to solid-state diodes is used. Alternatively, any solid state gamma camera known in the art (including those described in the above referenced prior art cameras) may be used. Alternatively, an NaI(Tl) or CsI(Tl) scintillation crystal coupled to a position sensitive PMT is used. Alternatively, a wide-angle, diverging hole collimator, is used in order to provide a larger field of view to compensate for the small size of the gamma camera.

Figure 4:
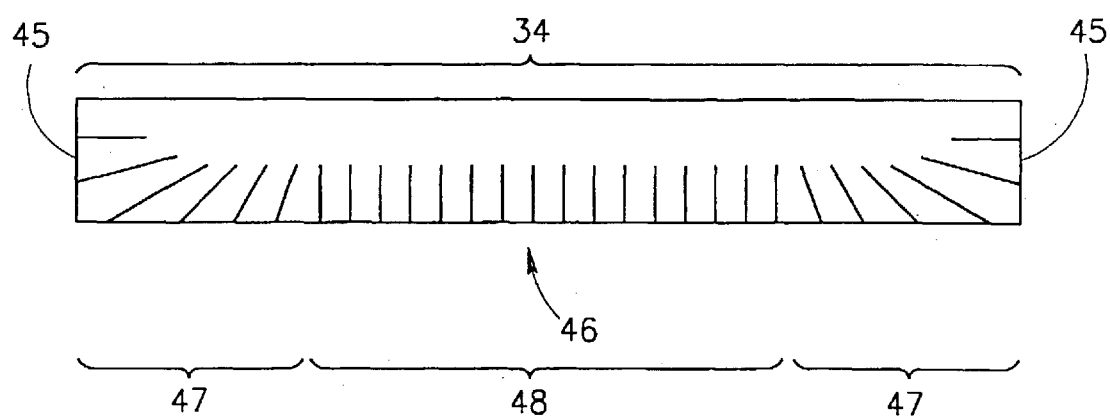
FIG. 4 is a schematic illustration of a diverging-hole collimator, for imaging of the field around the gamma camera, in accordance with a preferred embodiment of the present invention.

Reference is now made to FIG. 4 which is a schematic illustration of diverging-hole collimator 34, for imaging of the field around gamma camera 30. Preferably, collimator 34 comprises a circumference 45, a center 46, varying-angle septa 47 and right-angle, parallel-hole septa 48. Preferably, varying-angle septa 47 around circumference 45 begin with a very acute angle, perhaps even near 0°, for viewing the field adjacent to the gamma camera.

Preferably, the angle of varying-angle septa 47 increases gradually, for example, in small steps, so that the first several rows of septa around the periphery are divergent, and the septa near and at the center are at right angle to the axis of the collimator. In this manner, as the gamma camera is moved across the tissue, it views both the tissue directly below it and, with lower resolution, the tissue around it.

In some preferred embodiments of the present invention, gamma camera 30 comprises also a gamma counter or detector 50 (shown on FIG. 3) for example at the front of gamma camera 30. Counter 50 serves as a coarse probe. Preferably, counter 50 has a much higher efficiency than the spatially sensitive and energy sensitive detector 32. Therefore, counter 50 may lead the physician to areas that need close examination. Preferably counter 50 is provided with a limited field of view, within the field of view of camera 30, so as to aid in determining the direction with improved resolution.

Figure 5:
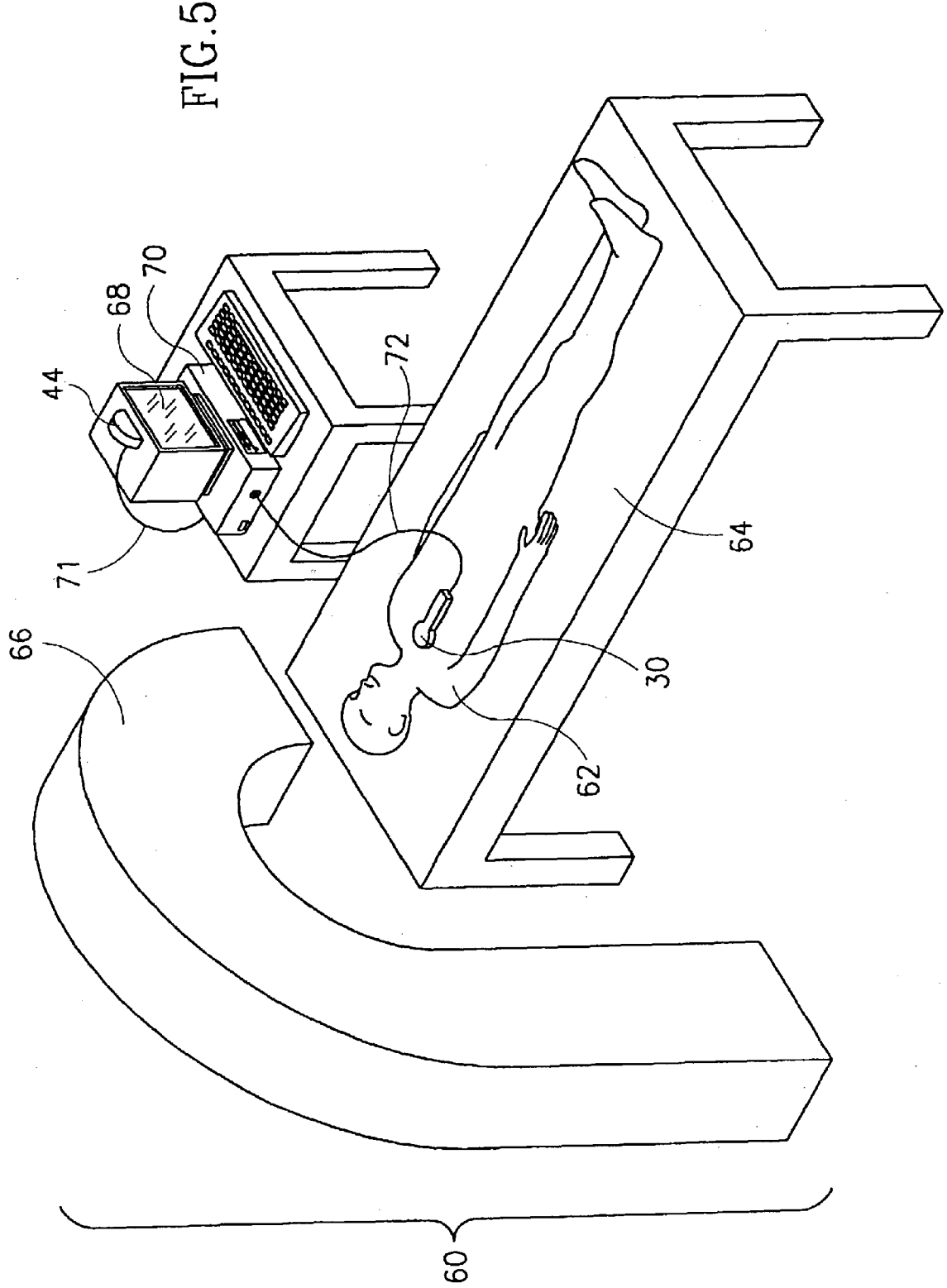
FIG. 5 is a schematic illustration of a hand-held gamma camera with a remotely readable spatial coordinate determining device, used in an operating room, in accordance with a preferred embodiment of the present invention.

Reference is now made to FIG. 5 which is a schematic illustration of a hand-held gamma camera 30 with a remotely readable spatial coordinate determining device 43, in an operating room 60, in accordance with a preferred embodiment of the present invention. Preferably, a patient 62 is lying on an operation table 64. A stationary imaging system 66, such as an x-ray machine, a CAT scanner or any imaging system as known in the art is used for referencing the coordinates of patient 62 with some known spatial coordinate system. Alternatively, radioactive markers on the patient are used for reference for camera 30. The patient image is displayed on a monitor 44, attached to a data acquisition computer 70.

Alternatively, a video image of the patient (or the area) may be used as an intermediary to match the nuclear image with CT or MR images from previous scans. Such matching is known in the art.

Event position information from gamma camera 30 are also sent to data acquisition computer 70. The coordinates of gamma camera 30 are sent via transmitter 42, receiver 44 and/or a cable 71. Therefore, images from gamma camera 30 can be superimposed on the patient's coordinate system, as displayed by stationary imaging system 66. In this manner, it is possible to image objects that are difficult to image by stationary imaging system 66, by getting very close to them with small, hand-held gamma camera 30, without losing the spatial positioning information that stationary imaging system 66 yields. The small camera can also be placed against an organ, even a moving organ.

Furthermore, since gamma camera 30 is easy to manipulate, it is possible to obtain images at different viewing angles, and in this manner, calculate the 3-D coordinate of a suspected lesion.

In a preferred embodiment of the invention, a gamma camera can be used to provide an indication as to whether all of a cancerous growth (or other selectively absorbing tissue or lesion) has been removed. In particular, before the growth is removed, the growth is imaged. After removal, an additional image of the same area is taken to determine if any of the tissue that took up the radiopharmaceutical remains in the body and where it is situated. Since the position of the probe during acquisition of both images is known, the images can be matched to determine whether any of the tissue tagged with the radiopharmaceutical has not been removed. In particular, a side by side comparison may be made. Alternatively or additionally a two color overlay may be displayed, with one color representing before and the other after.

The present invention has been described using non-limiting detailed descriptions of preferred embodiments thereof that are provided by way of example and are not intended to limit the scope of the invention. Variations of embodiments described will occur to persons of the art. Furthermore, the terms "comprise," include," and "have" and their conjugates mean, when used herein: "including but not necessarily limited to." The scope of the invention is limited only by the following claims:

What is claimed is:

1. A radiation camera system, comprising:
   a freely positionable radiation camera;
   a spatial coordinate determining system that determines the coordinates of the camera; and
   a receiver which receives the spatial coordinate information and imaging information, generated by the camera and provides imaging information referenced to a coordinate system not fixed in the camera.

2. A radiation camera system according to claim 1 and including:
   an image source;
   image alignment circuitry that receives the imaging information and an image from the source and references the imaging information to the image from the source; and
   a display that displays a radiation image based on the imaging information and the image from the source.

3. A radiation camera system according to claim 2 wherein the radiation image and the image from the source are displayed on a same coordinate system.

4. A radiation camera system according to claim 3 wherein the image from the source is a previous radiation image of a same portion of the patient.

5. A radiation camera system according to claim 2 wherein the image from the source is a CT image.

6. A radiation camera system according to claim 5 wherein the image from the source is a MRI image.

7. A radiation camera system according to claim 5 wherein the image from the source is an ocular image.

8. A radiation camera system according to claim 2 wherein the image from the source is a previous radiation image of a same portion of the patient.

9. A radiation camera system according to claim 1 wherein the radiation camera is a hand held camera.

10. A radiation camera system according to claim 9 wherein the spatial coordinate information is determined by the measurement of magnetic fields.

11. A radiation camera system according to claim 10 wherein the camera comprises sensors which measure electromagnetic fields generated by at least one fixed source to produce said spatial coordinate information.

12. A radiation camera system according to claim 11 including a receiver to which said spatial coordinate information is transferred, wherein said information is transferred to said receiver by wireless means.

13. A radiation camera system according to claim 11 and including a radiation detector having a sensitivity greater than that of the camera facing in a same direction as a field of view of the camera.

14. A radiation camera system according to claim 1 wherein the imaging information is transferred to a receiver from the camera by wireless means.

15. A radiation camera system according to claim 1 wherein the camera is a gamma camera.

16. A radiation camera system according to claim 1 wherein the camera is a beta camera.

17. A radiation camera system according to claim 1 wherein the camera is an Anger camera.

18. A radiation camera system according to claim 1 wherein the camera is a solid state camera.

19. A radiation camera system according to claim 1 including a position sensor mounted on the camera.

20. A radiation camera system according to claim 1 wherein the coordinate system is fixed in space.

21. A radiation camera system according to claim 1 wherein the coordinate system is referenced to a patient.

* * * * *